United States Patent
Schreiber et al.

(10) Patent No.: US 12,429,047 B2
(45) Date of Patent: Sep. 30, 2025

(54) TEST DEVICE FOR TESTING FUNCTIONS OF A PUMP

(71) Applicant: Fresenius Medical Care Deutschland GmbH, Bad Homburg (DE)

(72) Inventors: Lena Schreiber, Bad Homburg (DE); Sven Marten Czerwonka, Frankfurt (DE); Alexander Schroers, Frankfurt am Main (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 548 days.

(21) Appl. No.: 17/780,219

(22) PCT Filed: Dec. 2, 2020

(86) PCT No.: PCT/EP2020/084268
§ 371 (c)(1),
(2) Date: May 26, 2022

(87) PCT Pub. No.: WO2021/110747
PCT Pub. Date: Jun. 10, 2021

(65) Prior Publication Data
US 2022/0412343 A1    Dec. 29, 2022

(30) Foreign Application Priority Data

Dec. 4, 2019   (DE) .......................... 102019132946.9

(51) Int. Cl.
*F04B 51/00*    (2006.01)
*A61M 5/145*    (2006.01)
*A61M 5/168*    (2006.01)

(52) U.S. Cl.
CPC .......... *F04B 51/00* (2013.01); *A61M 5/1452* (2013.01); *A61M 2005/16863* (2013.01)

(58) Field of Classification Search
CPC ................. F04B 51/00; A61M 5/1452; A61M 2005/16863; A61M 1/342; A61M 1/3672;
(Continued)

(56) References Cited

U.S. PATENT DOCUMENTS

| 5,254,096 A | 10/1993 | Rondelet et al. |
| 5,272,917 A | 12/1993 | Pippert |

(Continued)

FOREIGN PATENT DOCUMENTS

| DE | 4000873 | 7/1991 |
| DE | 4220831 | 4/1994 |

(Continued)

OTHER PUBLICATIONS

International Search Report and Written Opinion in International Appln. No. PCT/EP2020/084268, mailed Feb. 26, 2021, 20 pages (with English translation).

*Primary Examiner* — Tarun Sinha
(74) *Attorney, Agent, or Firm* — Fish & Richardson P.C.

(57) ABSTRACT

The present disclosure relates to a test device to be inserted into the syringe receptacle of a pump, for example for a blood treatment apparatus, for testing at least one function of the pump and/or of the blood treatment apparatus. The test device includes a holding device for releasably holding the test device on the housing of the blood treatment apparatus. In addition, the test device includes at least one movable actuator and at least one electric motor arranged to directly or indirectly move said movable actuator or a section thereof.

10 Claims, 10 Drawing Sheets

(58) Field of Classification Search
CPC .......... A61M 2205/14; A61M 2205/18; A61M 2205/3306; A61M 2205/332; A61M 2205/50; A61M 2209/02; A61M 5/1458; A61M 5/1456

See application file for complete search history.

(56) References Cited

U.S. PATENT DOCUMENTS

| | | | |
|---|---|---|---|
| 5,785,926 A * | 7/1998 | Seubert | B01L 3/02 |
| | | | 73/864.22 |
| 5,943,633 A | 8/1999 | Wilson et al. | |
| 8,715,215 B2 | 5/2014 | Kopperschmidt | |
| 10,307,531 B2 | 6/2019 | Faulhaber et al. | |
| 2010/0250003 A1 * | 9/2010 | Nieboer | F16M 11/046 |
| | | | 356/402 |
| 2012/0065617 A1 * | 3/2012 | Matsiev | A61M 5/142 |
| | | | 73/61.61 |
| 2021/0052808 A1 | 2/2021 | Tanneberg et al. | |

FOREIGN PATENT DOCUMENTS

| | | |
|---|---|---|
| DE | 19536823 | 2/1997 |
| DE | 69315158 | 3/1998 |
| DE | 69613484 | 4/2002 |
| DE | 102007044413 | 3/2009 |
| DE | 102013004860 | 9/2014 |
| EP | 0492454 | 7/1992 |
| WO | WO 97/10859 | 3/1997 |
| WO | WO 97/25083 | 7/1997 |
| WO | WO 2019/193089 | 10/2019 |

\* cited by examiner

TEST DEVICE FOR TESTING FUNCTIONS OF A PUMP

CROSS-REFERENCE TO RELATED APPLICATIONS

The present application is the national stage entry of International Patent Application No. PCT/EP2020/084268, filed on Dec. 2, 2020, and claims priority to Application No. DE 10 2019 132 946.9, filed in the Federal Republic of Germany on Dec. 4, 2019, the disclosure of which are expressly incorporated herein in its entirety by reference thereto.

TECHNICAL FIELD

The present disclosure relates to a test device or pump test device. It further relates to a system as described herein and a method as described herein. It further relates to a pump and a blood treatment device.

BACKGROUND

Infusion pumps are usually used to administer a liquid drug to a patient, for example through a catheter or other access. The way the liquid is infused is controlled by the infusion pump, which may have different infusion modes, such as a continuous mode in which the liquid drug is infused continuously at a constant, comparatively low rate, or a bolus mode in which the infusion rate conveys or promotes at a comparatively high rate for a short period of time.

Infusion pumps typically need to be tested before delivery to ensure that they function properly. Typically, they are therefore connected to a testing device and manually prompted to convey fluid. This pumping process is typically triggered or initiated by a person performing the test by manually activating an input device associated with the infusion pump, such as a keyboard or a button on a graphical user interface.

SUMMARY

An aspect of the present disclosure is to describe a new type of test device. In addition, a system, a method, a pump and a blood treatment apparatus are also described herein.

This is achieved by a test device as described herein. It is also achieved by a system as described herein, by a method as described herein, by a pump as described herein, and by a blood treatment apparatus as described herein.

In all of the following statements, the use of the expression "may be" or "may have" and so on, is to be understood synonymously with "preferably is" or "preferably has," and so on, respectively, and is intended to illustrate embodiments according to the present disclosure.

Whenever alternatives with "and/or" are introduced herein, the person skilled in the art understands the "or" contained therein preferably as "either or" and preferably not as "and".

Whenever numerical words are mentioned herein, the person skilled in the art shall recognize or understand them as indications of a numerical lower limit. Unless it leads the person skilled in the art to an evident contradiction, the person skilled in the art shall comprehend the specification for example of "one" as encompassing "at least one". This understanding is also equally encompassed by the present invention as the interpretation that a numerical word, for example, "one" may alternatively mean "exactly one", wherever this is evidently technically possible for the person skilled in the art. Both are encompassed by the present disclosure and apply to all numerical words used herein.

Whenever spatial references like "top", "bottom", "left" or "right" are mentioned herein, these are to be understood in case of doubt by the person skilled in the art as spatial information with reference to the orientation in the here accompanying figures and/or to the arrangement of apparatus(es) according to the present disclosure when used as intended.

The test device according to the present disclosure is provided and suitable to be inserted into the syringe receptacle of a pump, e.g., an infusion pump, for example a heparin pump of a blood treatment apparatus. During use, the test device serves for testing at least one function of the pump and/or of the blood treatment apparatus being connected to the pump.

A pump, which may be tested for correct function by the test device as described herein, includes at least a pump drive and a pump spindle, which may be rotated around its longitudinal axis by the pump drive (e.g., an electric motor, such as a stepper motor). The pump also has a handle for abutting a piston flange of a syringe with liquid medication thereon. The pump spindle, which is in rotary connection with the pump drive, is connected to the handle in a form-fit and/or force-fit manner. This connection has the effect that when the pump spindle is rotated by the pump drive, the handle is displaced translationally, here upwards or downwards. To transform rotation into translation, a draw tube or draw rod may be used, alternatively another element. Thus, the pump spindle may have a first thread that engages with a second thread of the draw tube.

The pump also has a so-called handle with a clamping arrangement. The clamping arrangement includes at least a first spring and two clips for clamping the piston flange of the syringe between them. The clamping may be done against the spring force of the first spring. The clamping arrangement further includes at least one clamping lever for releasing the clamping. The at least one clamping lever is arranged so that it may be actuated against the spring force. If it is actuated, for example, the two clips connected to the at least one clamping lever open and release the piston flange or release its clamping. The handle serves to hold the piston flange in a form-fit and/or force-fit manner. If the piston flange, which is clamped between the clips of the clamping arrangement of the handle, is moved translationally together with the handle as the pump spindle rotates, this changes the volume of the syringe and liquid present in the syringe is dispensed or applied via the nozzle of the syringe.

The syringe holder of the pump further includes two wings. At least one of the wings includes at least one second spring for receiving a section of a syringe cylinder of the syringe between the wings against the spring force of the second spring.

The pump includes also a pushbutton switch or tactile sensor in its handle. The pushbutton switch is used to check whether the piston flange of a syringe is inserted into the clamping arrangement or not.

The test device includes a holding device. The holding device serves to releasably hold the test device on a surface of the blood treatment apparatus, e.g., on an outer wall of its housing, at least for the time during which the pump is tested using the test device.

Furthermore, the test device includes at least one movable actuator and at least one electric motor. The electric motor may be, for example, a servomotor, a stepper motor or an electromagnet. The electric motor is arranged to directly or indirectly rotate or translate the movable actuator or a section thereof. The movable actuator may be, for example, a spindle (with or without the movable draw tube), a rotatable rotary section, a movable core or the like.

The system for testing at least one function of a pump and/or of a blood treatment apparatus includes a test device as described herein.

The system further includes a computer. The computer may be, e.g., a user computer which is programmed, for example, to read and/or process inputs made by a user. It may optionally be programmed to convert the user's input or, for example, factory adjusted settings into individual test commands or into a complete test scheme with a large number of test commands, or to generate test commands based on the inputs or default settings. For this purpose, it may be in communication with the test device to cause it to perform test activities such as executing movements, etc.

A test scheme may also be understood as a check "program" or test "program", test scenario, test case, a situation to be tested or examined and may also be referred to as such.

The computer may be optionally programmed to allow the test device to—e.g., directly or indirectly—execute single predetermined test commands or the entire predetermined test scheme.

The computer may also optionally be programmed to receive parameters (alternative thereto: parameter values) transmitted by the blood treatment apparatus or read the parameters from the blood treatment apparatus. Parameters may be suitable to reflect the function of the blood treatment apparatus or of its pump, for example in the form of error messages, pump parameters, measured values and the like.

Measured values may, for example, indicate a conveyed volume delivered by the pump, an effected conveying rate, the size of a syringe inserted into the pump, and the like.

For example, the computer is programmed to transmit a test command to a control device of the test device, on the basis of which the spindle drive of the test device rotates the spindle of the test device in a first direction of rotation. A section connected to the spindle, e.g., a draw tube, is thereby moved in a first direction.

Alternatively or in addition to this, the computer is programmed to transmit a test command to the control device of the test device on the basis of which test command the spindle drive rotates the spindle of the test device in a second direction of rotation in order to move the section connected to the spindle, e.g., the draw tube, in a second direction, wherein the second direction is opposite to the first direction.

A further alternative or additional test command may be aimed at rotating at least one of the wings of the syringe holder of the pump about its axis of rotation by a first motor and a first actuator of the test device (as examples of the electric motor and of the at least one actuator respectively).

A further alternative or additional test command may be aimed to sufficiently actuate at least one of the clamping levers of the pump using a second motor and a second actuator in order to decouple the pump spindle from the pump handle.

A further alternative or additional test command may be aimed at actuating and/or releasing (i.e., not or no longer actuating) the push-button switch, e.g., directly or indirectly, by an electromagnet.

The control device is anyhow in signal communication with the computer or is prepared for same. It may receive for example the above-mentioned and/or optionally further test commands (or signals corresponding to them, e.g., in machine language) from the computer and, if necessary, control the motor(s) of the test device accordingly.

The method described herein serves to test at least one function of a pump and/or of a blood treatment apparatus which is connected to a pump.

The method encompasses providing a system as described herein as well as inserting the test device into the syringe receptacle of the pump which is to be tested.

The method optionally encompasses the input by a user via an input device, of at least one test command or a function of the pump or of the blood treatment apparatus, which function is to be tested, and, if appropriate, assigning one or more test commands or the entire test scheme with a plurality of test commands to this input, using for example the control device, the computer or the input device.

The method optionally encompasses actuating the blood treatment apparatus in to effect an activity of the pump.

The method optionally encompasses controlling the control device of the test device by the computer in order to execute, using the following steps, one or more of the test commands generated or transmitted by the computer:

controlling the spindle drive in order to rotate the spindle in a first direction of rotation;

controlling the spindle drive in order to rotate the spindle in a second direction of rotation, wherein the second direction of rotation is opposite to the first direction of rotation;

blocking or stopping the spindle drive in order to simulate a pump standstill;

supplying current and/or voltage to the electromagnet in order to directly or indirectly trigger or terminate an actuation of the pushbutton switch using the electromagnet;

disconnecting or releasing the electromagnet, which previously actuated the pushbutton switch, from a current or voltage in order to directly or indirectly end or trigger an actuation of the pushbutton switch;

controlling the first motor in order to rotate at least one of the wings about its axis of rotation using the first actuator; and/or controlling the second motor in order to actuate at least one of the clamping levers and/or in order to decouple the pump spindle from the handle of the pump, or vice versa, using the second actuator.

The method optionally encompasses retrieving parameters, that describe the activity of the pump, from the pump or from the blood treatment apparatus, and/or retrieving or reading out parameters that are output by the blood treatment apparatus in connection with the activity of the pump.

In this, parameters may be, for example, measured values, error messages, alarms, status reports, etc. The retrieving may be made using the computer or using an output device of the blood treatment apparatus or of the pump.

The method optionally encompasses evaluating the queried parameters based on predetermined criteria.

The method optionally encompasses outputting a result of the evaluation using an output device, e.g., for the information of the user and/or for his knowledge.

The pump as described herein is or has been tested using the test device as described herein, the system as described herein and/or the method as described herein.

The blood treatment apparatus includes a pump as described herein.

Embodiments may include one or several of the features mentioned supra or in the following. In this, the features mentioned herein may in any combination be subject-matter of embodiments, unless the person skilled in the art recognizes a specific combination as being technically impossible.

Whenever "programmed" or "configured" is mentioned herein, it is hence also disclosed that these terms are to be interchangeable.

Whenever an embodiment is mentioned herein, it is then an exemplary embodiment.

A controlling or actuating, whenever mentioned herein, may also be regulating or a regulation.

When reference is made herein to a signal communication or communication connection between two components, this may be understood to mean a connection that exists in use. Likewise, it may be understood that there is a preparation for such a signal communication (wired, wireless, or otherwise implemented), for example, by a coupling of both components, such as by pairing, etc.

Pairing is to be understood as a process that takes place in connection with computer networks in order to establish an initial link between computer units for the purpose of communication. The best-known example of this is the establishment of a Bluetooth connection, by which various devices (e.g., smartphone, headphones) are connected to one another. Pairing is sometimes referred to as bonding.

When it is disclosed herein that the subject-matter includes one or several features in a certain embodiment, it is also respectively disclosed herein that the subject-matter does, in other embodiments, explicitly not include this or these features, for example, in the sense of a disclaimer. Therefore, for every embodiment mentioned herein it applies that the converse embodiment, e.g., formulated as negation, is also disclosed.

In some embodiments, the test device includes a control device. It serves to control or to actuate the at least one electric motor or some or all of its electric motor(s) if several motors are provided. Alternatively, the test device is connected to such a control device. The control of the electric motors, if there are several ones, may be carried out for all of them together, separately, simultaneously or successively independently of each other and/or in individual cases, as far as specific motors are concerned, said control may not be carried out at all.

In several embodiment, the at least one electric motor is or includes a spindle drive, arranged for directly or indirectly rotating the spindle. For example, the electric motor may be or may include a stepper motor connected to the spindle, which is here an example of the at least one movable actuator. A, e.g., rigid coupling may be provided for coupling a motor shaft of the spindle drive to the spindle.

In some embodiments, the at least one electric motor is or includes a first motor, e.g., a servomotor, which may be provided as an alternative or in addition to the aforementioned spindle drive. The first motor may serve to rotate a first actuator as an example of the movable actuator. The first actuator may be arranged for directly or indirectly rotating a wing of the pump about the axis of rotation of the wing.

In some embodiments, the at least one electric motor is or includes, again alternatively or in addition to the aforementioned, a second motor, e.g., a servomotor. The second motor is provided for rotating a second actuator as an example of a movable actuator. The second actuator includes a rotary section with one or more receptacles for form-fit or force-fit reception of, e.g., one section of each of the clamping levers of the section and/or for actuating the clamping levers and/or for decoupling the spindle of the pump from the handle of the pump. The receptacles may be designed as slots, protrusions, steps, depressions, hooks, etc. They can optionally be shaped as a negative of the clamping lever or of the clamping lever ends.

In some embodiments, the at least one electric motor is or includes, again alternatively or additionally, an electromagnet, e.g., a lifting magnet. The electromagnet can include a coil and a movable core. The movable core may be moved by an electromagnetic field, which may be generated by the coil, and is therefore also understood here as an example of the movable actuator. The electromagnet is arranged so as to actuate or release the pushbutton switch, for example directly or indirectly (for example by a ramp or rocker, a lever, or the like), by moving the movable core in one direction or the other.

The at least one electric motor may thus be understood as a single motor or as a group of motors, e.g., such as those listed above, in any combination. The same applies analogously to the at least one movable actuator.

In some embodiments, the spindle of the test device is not self-locking and/or it is arranged as non-self-locking.

This may include various embodiments, as well as arbitrary combinations of embodiments. On the one hand, it may optionally be provided that the spindle is arranged so that it may be rotated without causing or opposing any significant resistance to such forced rotation. So, if the spindle is rotated in another way than by its spindle drive (e.g., by hand), the connection of the spindle with its spindle drive does not hinder or does not inhibit such a rotation. Such a constructive design may be achieved, for example, by a corresponding coupling and/or a corresponding design of the spindle drive.

On the other hand, it may, again optionally, be provided that a component which is arranged to be translationally moved by a rotation of the spindle (such as the draw tube mentioned herein) is engaged with the spindle such that the component may be moved along the longitudinal axis of the spindle (e.g., by hand)—wherein the spindle itself must rotate in order to even allow the movement of the component along the longitudinal axis—without the spindle resisting significantly to this movement or its rotation.

Combinations of the aforementioned embodiments are also optionally provided.

A non-self-locking spindle may thus permit a rotation of the spindle and/or a displacement of the component, being in rotary connection with the spindle, along the longitudinal axis of the spindle even if the rotation and/or the displacement is not caused or effected by the spindle drive but by other forces or other motors.

A non-self-locking spindle may advantageously allow a displacement of the component that is in rotary connection with it even at moments in which the spindle drive is not active and, therefore, does not cause rotation itself. Thus, due to its lack of self-locking, the spindle may also allow "passive" rotation of the spindle, i.e., rotation not caused by the spindle drive, which is forced by the displacement of the component. "Passive" may be synonymous with co-conveyance by the pump, in which it is not the spindle drive of the test device, but the pump drive that moves sections of the test device.

In contrast thereto, "active", as used herein, may be synonymous with a rotation of the spindle initiated by the spindle drive. An "actively" driven spindle may simulate, e.g., supposed conveyance rates which are faked or pretended by the activity of the test device.

A significant resistance, as used herein, would be achieved if the corresponding apparatuses, motors, drives and the like of the pump or of test device were not strong enough to cause rotation of the spindle and/or translation of the component connected to the spindle, and/or if such an action by them would result in an error message or in another reaction, e.g., respectively on the pump control side of the blood treatment apparatus.

In some embodiments, the control device of the test device is programmed or configured to order rotate the spindle in a first direction of rotation by the spindle drive.

Alternatively or additionally, the control device is programmed or configured in order to rotate the spindle in a second direction of rotation being opposite to the first direction of rotation by using the spindle drive.

Alternatively or additionally, the control device is programmed or configured in order to directly or indirectly actuate and/or release the pushbutton switch by using the electromagnet.

Alternatively or additionally, the control device is programmed or configured in order to rotate at least one of the wings of the syringe holder about its axis of rotation by using the first motor and the first actuator.

Alternatively or additionally, the control device is programmed or configured in order actuate at least one of the clamping levers of the pump to decouple the pump spindle from the pump handle by using the second motor and the second actuator In several embodiments, the second actuator is multi-jointed or has several articulations or joints or is multi-axis or designed as at least one spherical joint or includes at least one such component.

The second actuator may consist of several components, for example two of which may be designed as a ball joint. In various embodiments, it may include one or more spherical joints.

The ball joints may compensate for the horizontal and vertical differences that occur when the clamping levers are actuated.

The ball joints may already be produced as an enclosed ball, for example by using a 3D printer, in order to ensure that the ball is firmly seated in the joint and still has plenty of freedom of movement, which may benefit the accuracy of the test device.

In some embodiments, the control device is or includes a signal transmission device. The signal transmission device serves to transmit the test commands (or a test scheme), generated by a computer, to the electric motor of the test device, wherein the computer is configured or provided to generate at least one test command.

In some embodiments, the control device is or encompasses a Raspberry Pi.

The computer and/or the control device may be programmed to have a series or sequence of predetermined test commands or test schemes executed.

The test commands may be stored in a storage device, a software and/or a computer program. A user may select from them single test commands or arbitrary combinations therefrom. For example, he may be interested in only an occlusion test, in which the spindle drive not only does not rotate the spindle, but also blocks rotation by the activity of the pump drive, thus simulating, for example, an occlusion of a heparin line connected to a syringe. Alternatively, the user may have the plurality of possible test commands processed in whole or in part.

In some embodiments, the system further includes a blood treatment apparatus with a pump.

The statements made above regarding the components of the pump of the test device also apply analogously to the pump of the system. The description is omitted here to avoid repetition.

In some embodiments of the system, the test device is designed to be slid, set up, or inserted on at least one bracket of the blood treatment apparatus, with which it may be fixed to the housing of the blood treatment apparatus. Alternatively, it is slid, set up, or inserted.

In this, the test device may be designed such that a form-fit connection, a frictional connection and/or a force-fit connection takes place due to sliding it on. This may be sufficient to hold the test device securely on a syringe receptacle. For example, no further holding devices are necessary in these embodiments.

In other embodiments, instead of or in addition to the above-mentioned connection between the test device and the housing, holding devices may be provided, such as clip and/or latching devices, hook and/or magnetic connections and/or the like.

In several embodiments of the method described herein, the evaluation may include calculating sums, differences, products and/or quotients, checking results or values and/or comparing them with expected values, ranges, expected results.

In some embodiments, a plurality of predetermined test commands or test schemes may be executed automatically. This applies to single test commands as well as to entire test schemes.

In some embodiments, the method may take place when manufacturing the pump or the blood treatment apparatus.

In several embodiments, the blood treatment apparatus includes a blood pump and/or is connected to an extracorporeal blood circuit.

The extracorporeal blood circuit may have a first line, e.g., in the form of an arterial line section, which is in fluid communication with a blood treatment device, e.g., a blood filter or dialyzer. The blood filter includes a dialysis liquid chamber and a blood chamber, which are separated from each other by a mostly semi-permeable membrane. The extracorporeal blood circuit further includes at least one second line, here in the form of a venous line section. Both the first line and the second line may serve to be connected to the patient's vascular system.

The blood treatment apparatus may be designed as a dialysis apparatus, hemodialysis apparatus, hemofiltration apparatus, or hemodiafiltration apparatus, e.g., as an apparatus for the chronic renal replacement therapy or the continuous renal replacement therapy (CRRT).

In some embodiments, the manipulation of sensors of the pump (e.g., pushbutton switch, light barrier(s), position meter (linear potentiometer)) may be used to transmit correct, or deliberately false, signals to the blood treatment apparatus for testing purposes. Alternatively or in addition, besides standstill and predetermined conveying rates, further application scenarios or error cases may be simulated and tested, for example bolus delivery, reverse delivery or the like.

In several embodiments, the test device is capable of manipulating the sensors of the pump and/or of the blood treatment apparatus. This may, for example, simulate the insertion of an incorrect syringe size or the unauthorized removal of the syringe from the syringe cavity during a blood treatment.

In some embodiments, the systems described herein may advantageously be used to simulate all operating states, including all error states. The reaction of the pump or of the blood treatment apparatus to this simulation may be evaluated.

The simulation of errors with regard to the deviation of the conveying rate may be important, e.g., since the permanent self-control of the conveying rate can achieve the desired treatment success. The blood treatment apparatus can "notice" during a treatment session if its pump is pumping too quickly, too slowly, in the wrong direction, or not at all. Such incorrect conveyances and closure or blocking scenarios, e.g., of the heparin line, which should lead to a standstill alarm, are simulated in some embodiments by the test device and the reaction of the device or blood treatment apparatus under test is checked thereupon.

Moving the handle at a speed other than that which would correspond to the conveying rate set on the pump or on the blood treatment apparatus may be made possible by opening the clamping levers and decoupling the handle from the spindle or from the draw tube. Without such decoupling, the handle would be coupled to the spindle of the heparin pump via the draw tube in a forced guidance, which on one hand would prevent the execution of a series of the test commands mentioned herein. On the other hand, moreover during the execution of some test commands (e.g., when testing for occlusion, in which the handle is to be held stationary by the test device and prevented from moving), tensions occur between the components, which could lead to the destruction of the test device or pump.

In some embodiments, the test device is designed such that a backward or reverse pumping may be simulated using it or therewith.

In several embodiments, the test device does not encompass any measuring sensors, for example for force, pressure, and/or path.

In some embodiments, the test device does not encompass a volume accuracy testing unit.

In several embodiments, the test device does not encompass an occlusion device by which, for example, the lumen of a fluid line would be occluded.

In some embodiments, the test device does not encompass a valve.

In several embodiments, the test device does not cause or prompt the pump to perform a conveying behavior and/or does not intervene in or interfere with its control.

In some embodiments, the test device does not encompass a hydraulic connection.

In several embodiments, the test device does not encompass a test liquid.

In some embodiments, the test device does not encompass a fluid line and/or a fluid reservoir, e.g., a syringe reservoir for receiving a drug.

In some embodiments, the test device is not a syringe, e.g., not a disposable syringe.

In some embodiments, the test device does not perform a spindle movement (as an imitated conveying movement) against a spring force.

Some or all of the embodiments may have one, several, or all of the advantages mentioned above and/or below.

The test devices described herein advantageously allow the automatic testing of a pump. The at least one electric motor controlled by the control device may, together with the at least one movable actuator, check at least one function of the pump automatically.

The test devices described herein advantageously allow a number of different tests to be carried out on the pump. In this, it is possible to determine whether the pump and/or the blood treatment apparatus controlling the pump detects supposed disturbances or malfunctions, which the test device imitates.

A further advantage may be that the test devices may be used to test the hardware and software not only of the tested pump, but also of the blood treatment apparatus controlling the pump with regard to functionality and safety. Corresponding indications, which can also differentiate between the pump and the blood treatment apparatus as the cause of the specific test result, can also be provided, as can their output, e.g., by the output device. This also further indirectly increases patient safety.

Advantageously, the test devices may imitate the behavior of a real (e.g., disposable) syringe so realistically that the control of the pump or of the blood treatment apparatus cannot distinguish between the real syringe and the test device. In this way, both the reaction to the insertion of a supposedly inserted syringe and potential error states of the system may be tested or detected.

Both a syringe which is to be conventionally inserted for a check or for a test and a set of hoses used for the same purpose may be advantageously replaced by simulation models like the test devices described herein. This may help to save costs required for these components while testing the pump.

A further advantage of the test devices described herein may be that deliberately induced or caused error states may be evaluated by the software. This may advantageously increase the safety of the blood treatment and hence also the patient's safety.

By using movable actuators, checking the functional chain in which errors may occur, which are solely caused by the syringe pump, may be advantageously extended by the real influence of the corresponding components beyond the syringe pump and up to the function of the mechanics and sensor technology of the blood treatment apparatus. In addition to testing the pump as such, the hardware and/or software of the blood treatment apparatus may thus also be tested, for example to determine when errors in connection with the pump activity are noticed and how these are communicated.

Furthermore, by using the test devices described herein, more intensive and more extensive tests may be carried out on the blood treatment apparatus or on its pump, due to, amongst others, achieving a higher degree of automation. For example, tests may be repeated several times without much effort. This advantageously leads to an improvement of the quality and safety of the blood treatment apparatus and, in connection therewith, also of the quality and safety of the blood treatment. Indirectly, this results in increased patient safety.

An advantage of the test devices described herein may further be that the test device may be connected to the already existing test setup for endurance runs. This testing may thus be carried out more efficiently and/or more accurately.

Furthermore, the test devices described herein may advantageously be adapted or matched to a program, referred to here as TET, in order to run test cases automatically, for example in the form of test schemes. In this, the TET is a program with which test cases may be automatically simulated in a computer-controlled manner. For this purpose, the test schemes and/or test scenarios with the corresponding test commands are written, for example, in a ready-made Excel sheet. The language and form may be based on the Python programming language, but it can also be operated by people without programming knowledge.

BRIEF DESCRIPTION OF THE DRAWINGS

In the following, the present invention is exemplarily explained based on the accompanying drawings in which identical reference numerals refer to the same or to identical components. In the figures, the following applies.

DETAILED DESCRIPTION

Figure 1:
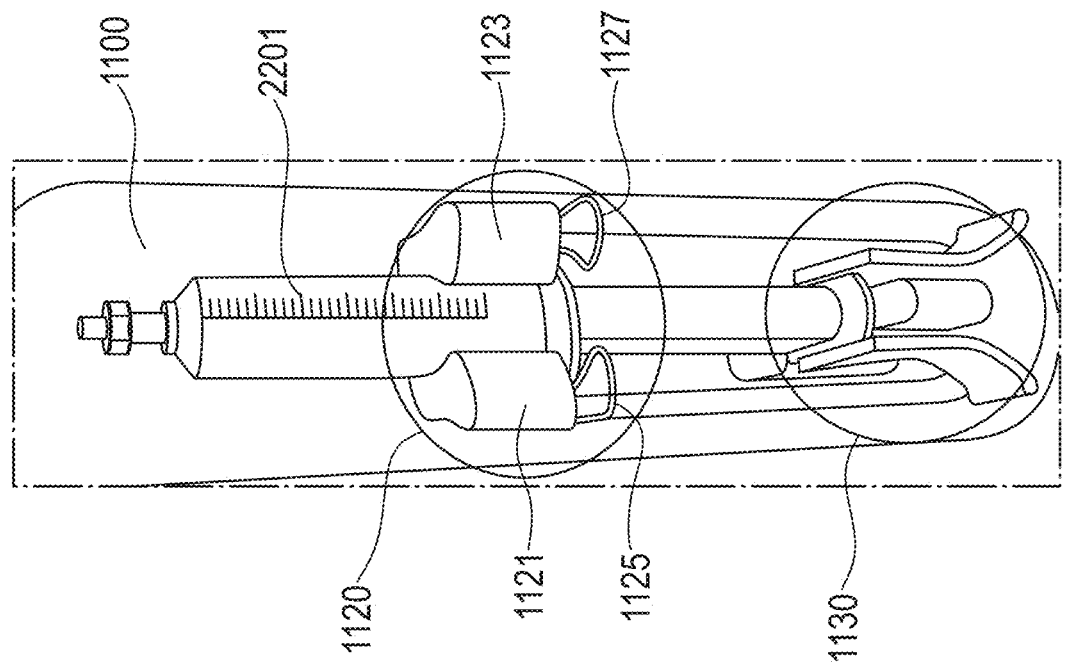
FIG. 1 shows an exemplary embodiment of the mechanics of a pump, on the left in a schematic representation, on the right in an installed state with an inserted syringe.
Figure 1:
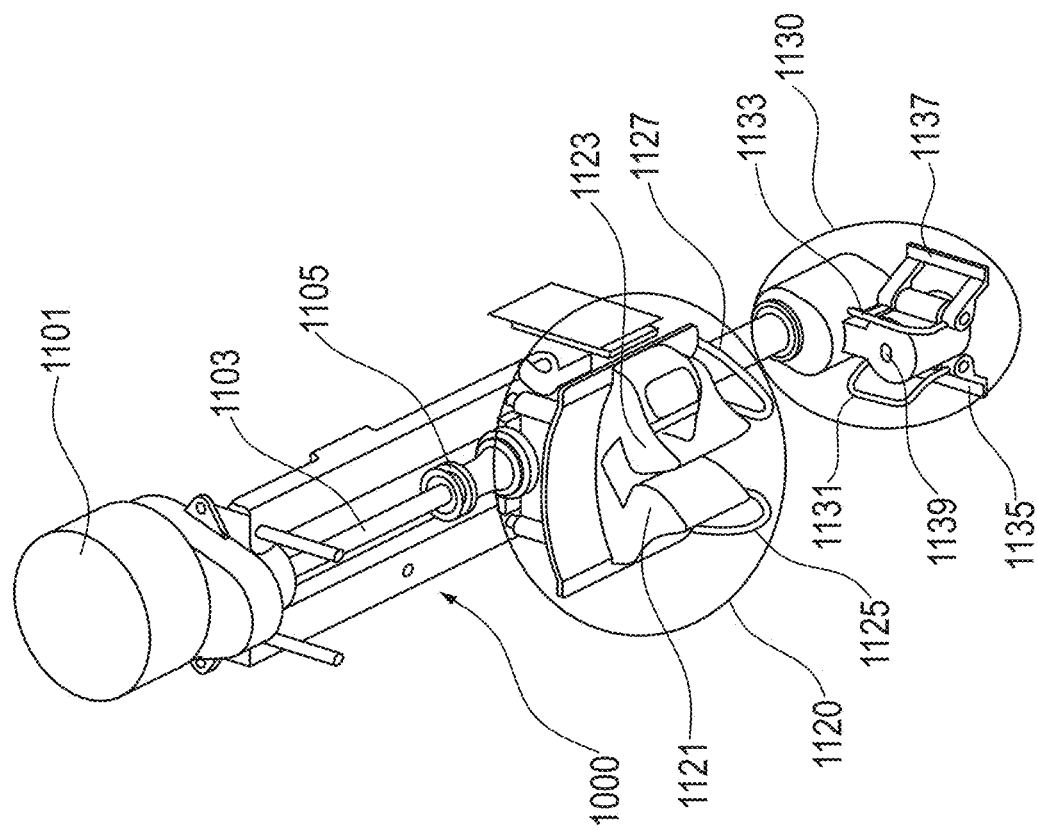

FIG. 1 shows an exemplary embodiment of a pump 1000, e.g., an infusion pump. The pump 1000 can be, for example, designed as a heparin syringe pump. The pump 1000 has a syringe cavity or syringe receptacle 1100 (see right). The pump 1000, e.g., has been tested by the method as described herein.

The heparin syringe pump 1000 includes a pump drive 1101 connected to a pump spindle 1103, and a draw tube 1105 which is in rotary connection with the pump spindle 1103.

Figure 2:
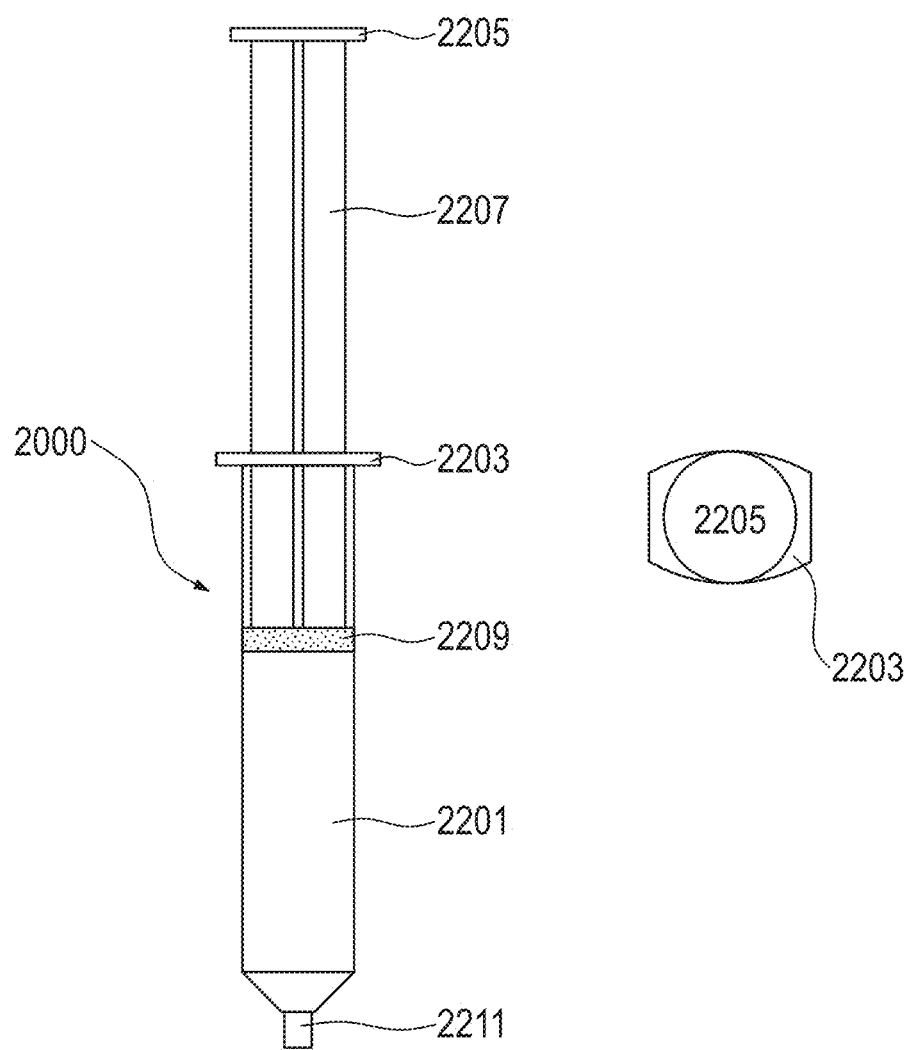
FIG. 2 shows an exemplary embodiment of a syringe.

The pump 1000 includes a syringe holder 1120, which in turn includes a left wing 1121 and a right wing 1123. The syringe cylinder 2201 of a syringe 2000, here exemplarily a heparin syringe, as shown in FIG. 2, is received between them, when the heparin syringe pump 1000 is in use. At least one of the two wings 1121, 1123 may be rotatably mounted and provided with a return spring. The distance between the two wings 1121, 1123 may thus adapt to the outer diameter of a syringe cylinder 2201 of the heparin syringe 2000 actually received between them. Since the two wings 1121, 1123 clamp the syringe cylinder 2201 between them, they may also be described as tension levers.

One or both of the wings 1121, 1123 may each have one or more light barriers which serve to determine the diameter of the syringe cylinder 2201 inserted between the two wings 1121, 1123. Thus, an interrupter may be provided which, in the case of, e.g., two light barriers, either one or both of the two light barriers interrupts or obscures depending on how far the relevant wing 1121 or 1123 had to be turned around its own axis of rotation in order for the syringe cylinder 2201 to find space between the two wings 1121, 1123.

Below the wings 1121, 1124, the syringe holder 1120 includes two brackets 1125, 1127. A cylinder flange 2203 of the syringe 2000 (see FIG. 2) is plugged between them and the underside of the wings 1121, 1123 when the syringe 2000 is inserted into the pump 100.

FIG. 1 further shows a handle 1130 with two clips 1131 1133, each of which merges into a clamping lever 1135, 1137.

The two clips 1131, 1133 are each rotatably mounted and connected to a return spring. The two clips 1131, 1133 are spaced apart from each other or include a distance between them. This distance may, using the two clamping levers 1135, 1137, be increased against the restoring force of the return springs, not shown, by pressing the two clamping levers 1135, 1137 towards each other. If the distance between the two clips 1131, 1133 is sufficiently large, the piston flange 2205 (FIG. 2) of the syringe 2000 inserted into the syringe cavity 1100 may be inserted between them. The piston flange 2205 is jammed between them when the clamping levers 1135, 1137 are no longer held or moved against the restoring force but rather move apart again due to the restoring force, whereby the clips 1131, 1133 are moved towards each other. The piston flange 2205 is thus held or jammed between the clips 1131, 1133.

A pushbutton switch 1139 can be seen between the clips 1131, 1133. It is pressed through the piston flange 2205 when the syringe 2000 is inserted. The pushbutton switch 1139, which is connected to a corresponding electronic circuit thus serves as a sensor which checks whether a syringe 2000 is inserted or not.

The pushbutton switch 1139 is optionally a touch switch, which requires a certain force to be actuated. Other sensors which are, e.g., not actuated by force, rather are designed, for example as light barriers, to check the presence of the piston flange 2205 are also encompassed by the present disclosure.

During an exemplary use of the heparin syringe pump 1000, heparin administration proceeds as follows.

In this embodiment, if both the light barrier(s) of the wing 1121 and the pushbutton switch 1139 have determined that a syringe 2000 is inserted in the syringe cavity or syringe receptacle 1100 of the heparin pump 1000, a heparin administration by the syringe 2000 is initiated by the pump 1000. The heparin administration follows a setting (e.g., flow rate) which may be set on the heparin pump 1000 or on a blood treatment apparatus 5000 connected to it (see FIG. 8), here a dialysis apparatus.

For the administration of heparin from the syringe 2000, the pump drive 1101, which may be designed as a stepper motor, may be controlled, e.g., according to specifications or settings present by the blood treatment apparatus 5000.

The stepper motor rotates the pump spindle 1103, which therefore rotates the longitudinally displaceable draw tube 1105 (in FIG. 1 in a an up-down direction) on which lower end the handle 1130 is fixed. If the pump spindle 1103 rotates, it indirectly pulls the handle 1130 upwards, i.e., towards (and against) the brackets 1125, 1127 or towards (and against) the syringe holder 1120. The distance between the handle 1130 and the syringe holder 1120 is shortened, and the syringe 2000, which is fixed in both the handle 1130 and the syringe holder 1120, is also shortened in that the syringe piston 2207 is pushed, gradually and based on the set or determined heparin rate, into the syringe cylinder 2201 while dispensing heparin through the nozzle 2211.

The heparin administration is monitored, for example, on the basis of the values of a linear potentiometer, e.g., continuously. In this, both the accuracy of the conveying rate and the direction of rotation are checked very precisely. At a predetermined time interval (timeslice), for example every 100 ms, the target position of the syringe is calculated depending on the selected syringe type, e.g., with an accuracy of 1 pl, and compared with the actual position detected by the linear potentiometer. Deviations exceeding a tolerance limit over a defined number of timeslices lead to error messages, and/or the pump is switched off by a protection system.

Warning messages or alarms occur, for example, if there is, amongst others, no anticoagulation, wrong syringe size, missing or empty syringe, wrong operating or operation action, or unexpected conveying deviation. An incorrect operating action is, for example, the removal of the syringe during the blood treatment, i.e., not during a syringe change required for inserting a full syringe. During normal use, the user is regularly guided throughout the syringe change process via a menu on the blood treatment apparatus. A removal of the syringe from the syringe cavity is detected or realized when the clips at the handle are opened by the user by pressing the clamping levers and thus, by this movement, pushing a lever upwards, which causes a mechanical decoupling of the handle from the pump spindle via a gear wheel. This results in a free positioning of the syringe piston along the conveying path, which should only occur when changing the syringe(s). Changing the position of the handle without selecting the above-mentioned menu for syringe change will result in an alarm. Whether such an alarm would go off correctly can be checked by the test device as described herein.

A stepper motor, which may be used for example for the pump drive 1101, may have a tightly fit stator and a rotatable rotor. The rotor may be, for example, a permanent magnet. The stator may be constructed from surrounding electromagnetic pole shoes, usually coils with iron cores. By selective or targeted control of the coils, a defined electromagnetic field is created, according to which the rotor aligns itself. This results in a stepwise rotation of the rotor. If the direction of the current flow through the coils is changed, the polarity of the stator is reversed and the stepper motor turns the motor shaft and a pump spindle connected to it via a coupling in the opposite direction.

FIG. 2 shows an exemplary embodiment of a syringe 2000.

In addition to the components already mentioned for FIG. 1, the syringe 2000 includes a syringe cylinder 2201, cylinder flange 2203 and piston flange 2205, a syringe piston 2207 with a piston stopper 2209 with a circumferential seal and a syringe neck or syringe head with a nozzle 2211.

Figure 3:
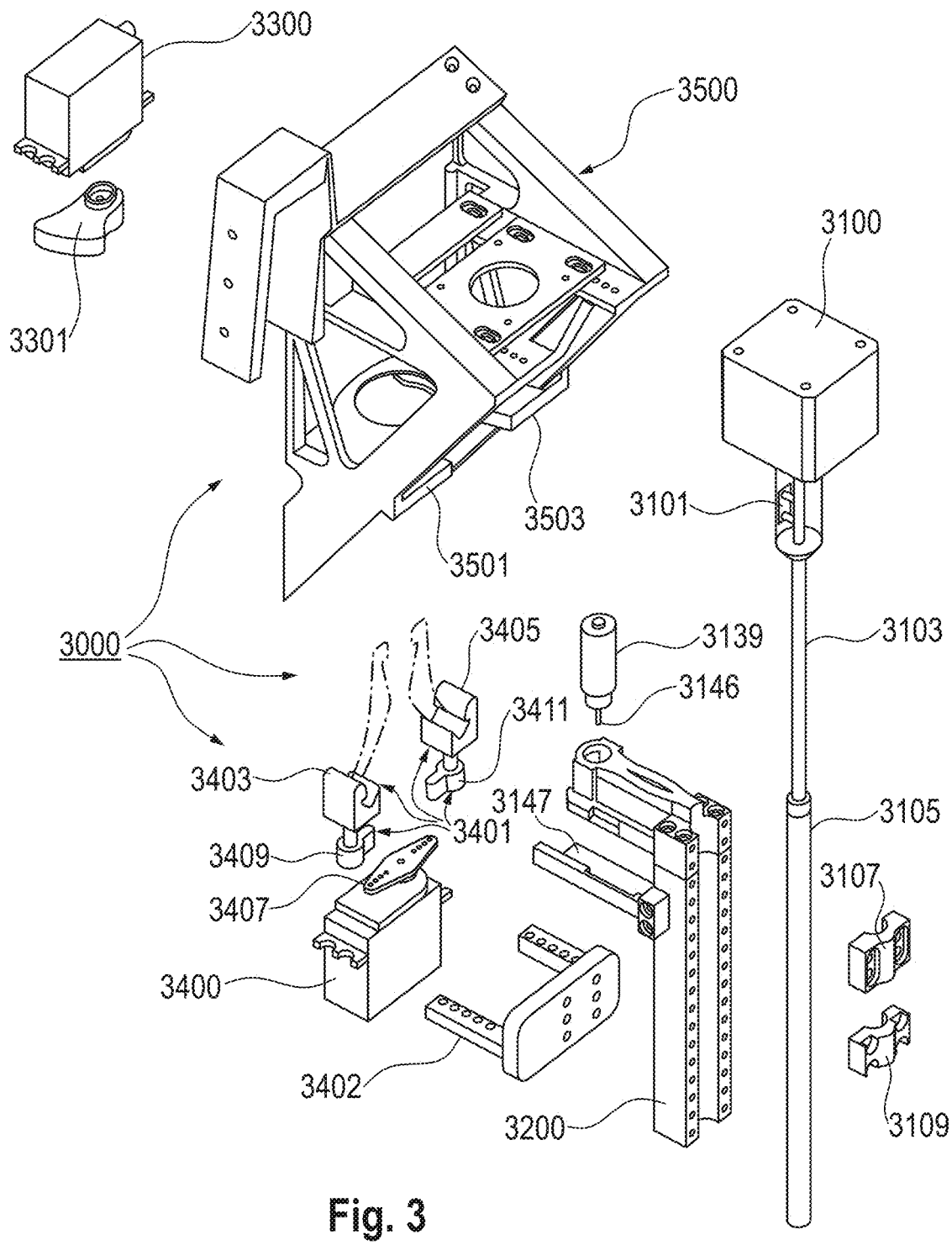
FIG. 3 shows a first embodiment of the test device in a very simplified exploded view.

FIG. 3 shows a highly simplified first embodiment of the test device 3000 in an exploded view.

On the right, an optional spindle drive 3100 can be seen, which is here exemplarily designed as a stepper motor. The spindle drive 3100 or its motor shaft is connected to a spindle 3103 via a coupling 3101, which may be rigid. By a thread, spindle 3103 is inserted in a draw tube 3105, which may move relative to spindle 3103. When the spindle drive 3100 turns the spindle 3103 by the coupling 3101, the spindle 3103 rotates in the draw tube 3105 and, depending on the direction of rotation, either pulls the draw tube 3105 upwards or pushes it downwards (each with respect to FIG. 3).

The spindle 3103 can be designed and/or arranged as non-self-locking.

The draw tube 3105 can connected, e.g., by fastenings 3107 and 3109, in a rotation-fixed manner to a carrier 3200, which may also carry an electromagnet 3139, described in more detail below, and a ramp 3147.

An optional first motor 3300, e.g., a servomotor, which may be part of the test device 3000, is shown at the top left.

Servomotors are electric motors that allow control of the angular position of their motor shaft as well as the rotational speed and acceleration. They usually include a sensor for determining the above-mentioned values.

The first motor 3300 may be connected to a first actuator 3301, here exemplarily a negative of a wing 1121 of the heparin pump 1000, see FIG. 1. In the present example, the first actuator 3301 is rotatably connected to the first motor 3300 via the first motor 3300. This arrangement serves to rotate the wing 1121 of the heparin pump 1000 on request and thus imitates the presence of a syringe, the diameter of which may be determined by the light barrier described herein. Different angular rotations of the first actuator 3301 by the first motor 3300 thus imitate syringes of different diameters.

FIG. 3 shows an optional second motor 3400 and a fastening 3402, with which the second motor 3400 may be fastened to a carrier 3200.

The second motor 3400 is connected by a receptacle 3403 for a lower end of the clamping lever 1135 and by a further receptacle 3405 for a lower end of the clamping lever 1137. With the help of the receptacle, the ends of the two clamping levers 1135, 1137 (indicated by dotted lines in FIG. 3) inserted in it may be pressed towards each other against a spring force. If they are pressed towards each other, the two clips 1131, 1133 hence open, see FIG. 1.

In the example in FIG. 3, the two receptacles 3403 and 3405 are moved by a rotary section 3407 which is connected in a rotation-fixed manner to a motor shaft of the second motor 3400.

The two receptacles 3403 and 3405 may each be equipped with or connected to a rotary joint, e.g., the spherical sections 3409 or 3411, respectively. These allow the two receptacles 3403 and 3405 to maintain the position or angular position relative to each other as shown in FIG. 3, even if they are brought closer together in a side view by rotating the rotary section 3407, with which both rotate. In addition, FIG. 3 shows a holder 3500, also referred to herein as a holding device, which serves to hold the aforementioned elements in the assembled state of the testing device 3000 (see FIG. 4) and which in turn is connectable to a housing 5001 of the dialysis apparatus 5000 (see FIG. 8). Optionally, no further device is provided in addition to the holder 3500 which further device would serve to fix the test device 3000 stationary to the housing 5001 of the dialysis apparatus 5000 or to the heparin pump 1000.

For fixing the holder 3500 of the test device 3000 to the dialysis apparatus 5000, the latter may, purely exemplarily, have inserts or other receptacles or connections by which it may establish a form-fit and/or a force-fit connection with for example the brackets 1125, 1127 of the heparin pump 1000.

In some embodiments, the holder or holding device 3500 is alternatively or additionally, a sufficiently strong magnet.

In the example of FIG. 3, there are two slots 3501 and 3503 of the holder 3500, into which the brackets 1125, 1127, see FIG. 1, may be inserted through a front side open towards the (in relation to FIG. 3) first motor 3300. The inserted state may be seen in FIG. 5.

The two slots 3501 and 3503 may be part of the holder 3500, which is optionally triangular in a side view. On the one hand, the triangular shape advantageously allows two contact points, which the holder 3500 and the housing 5001 of the dialysis apparatus 5000 have in common, to be relatively far apart, which is mechanically advantageous for the stability of the test device 3000 in use. On the other hand, the triangular shape allows for the holder 3500 to have as little weight as possible and/or to require as little installation space as possible.

The holder 3500 may be provided as part of the test device 3000. It allows the test device 3000, in order to imitate a syringe, to be inserted, at least in sections, into the syringe cavity or receptacle 1100 of the heparin pump 1000, which is seated on the housing 5001 of the dialysis apparatus 5000, and may, thereby, be held stationary on the housing 5001.

Figure 4:
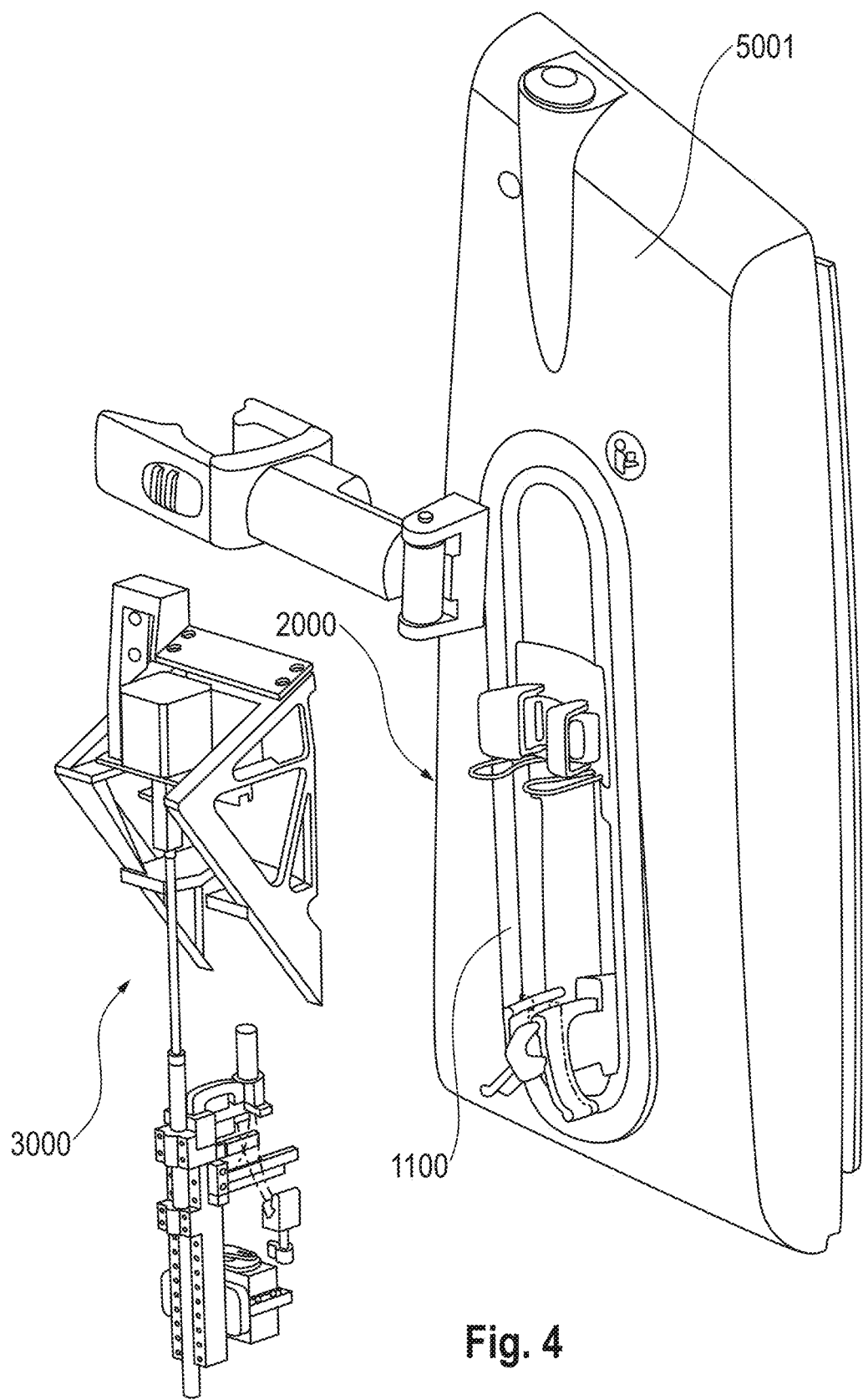
FIG. 4 shows the test device of FIG. 3 in the assembled state and the syringe pump with syringe cavity.

The assembled state of the components of the test device 3000 shown in FIG. 3 is shown in FIG. 4.

An exemplary spindle 3103 has a pitch of 5 mm.

For example, the spindle drive 3100, as a stepper motor, has a step size of 0.18°, which corresponds to 200 steps per revolution in full step mode and 1600 steps in microstep mode of the stepper motor.

In some implementations, the control of the spindle drive 3100 is not more than 1 ms per motor step.

The spindle drive 3100 may be designed to be blocked, for example by interfering in its control. If the spindle drive 3100 is blocked, its spindle 3103 cannot be turned, even by external forces or motors. If this is the case, the handle 1130 cannot be moved by the pump drive 1101 of the pump spindle 1103. As a result, when trying to convey heparin, the dialysis apparatus 5000 should detect resistance from the lack of conveyance movement of the handle 1130 and conclude that an occlusion has occurred.

The at least one electric motor in the example of FIG. 3 is thus to be understood as a combination of the first motor 3300, second motor 3400, spindle drive 3100 and electromagnet 3139.

The at least one movable actuator in the example of FIG. 3 is therefore to be understood as a combination of first actuator 3301, second actuator 3401, spindle 3103 and movable core 3143.

FIG. 4 shows the test device 3000 of FIG. 3 in the assembled state. The test device 3000 is shown in front of the syringe cavity 1100 of the heparin pump 1000 of the dialysis apparatus 5000, immediately before it is inserted into the syringe cavity 1100.

Figure 5:
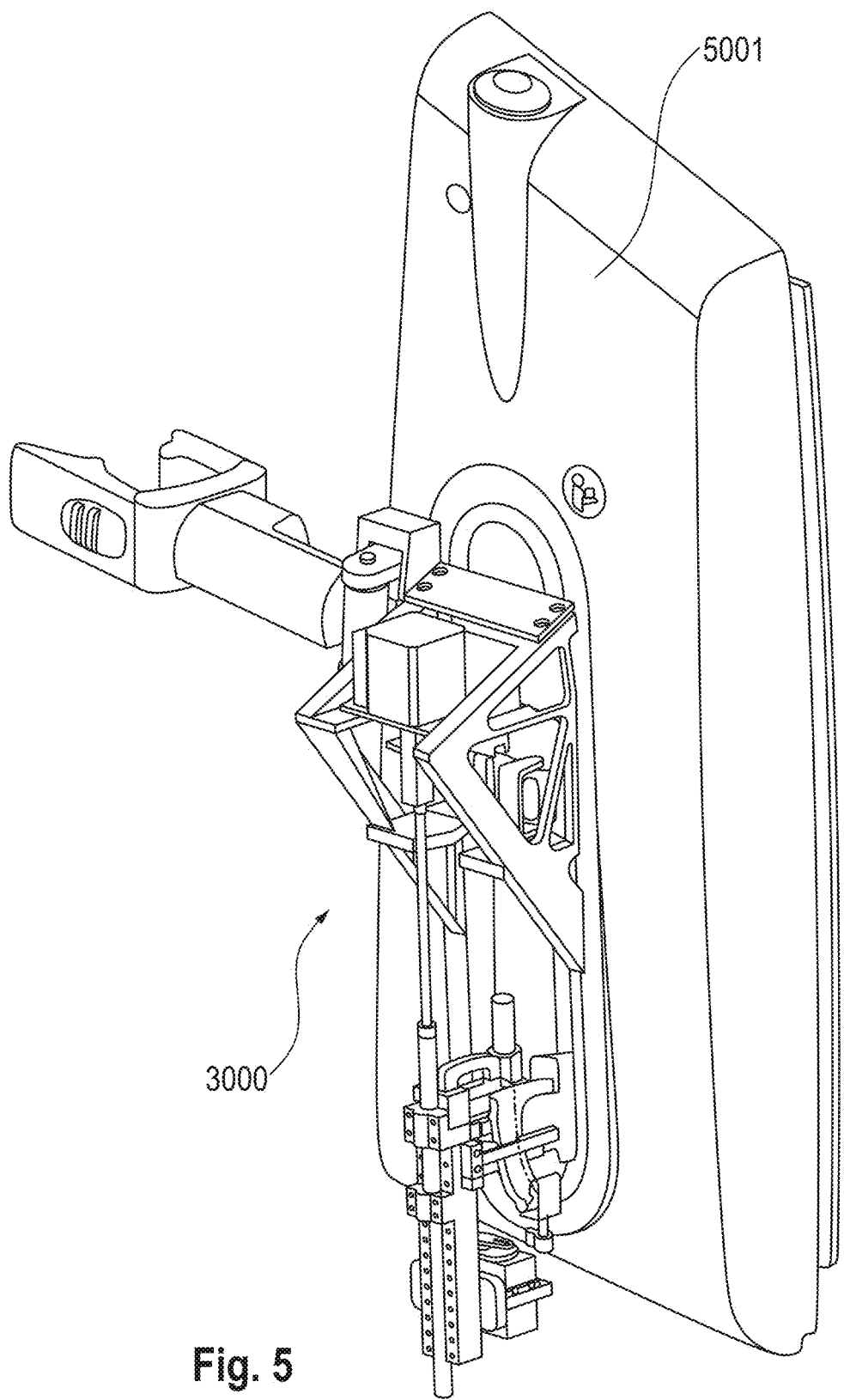
FIG. 5 shows the test device of FIG. 4 inserted in the syringe cavity of the pump.

FIG. 5 shows the test device 3000 of FIG. 4 at the housing 5001 of the dialysis apparatus 5000, inserted in or on the syringe cavity 1100 of the heparin pump 1000.

Figure 6:
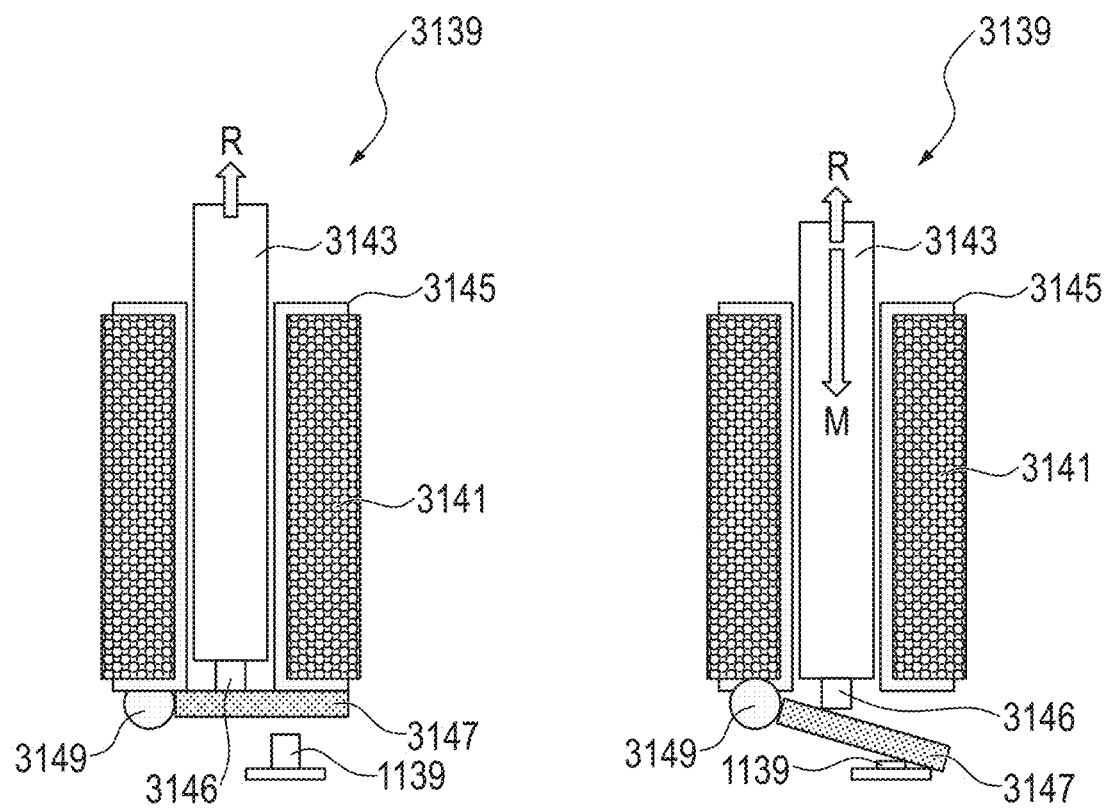
FIG. 6 shows an example of an arrangement with an electromagnet and a ramp of the test device in a section.

FIG. 6 shows an example of an arrangement with an electromagnet 3139 and a ramp 3147 of the test device 3000 in a schematically highly simplified sectional illustration.

The electromagnet 3139 is used by the test device 3000 to press or actuate the pushbutton switch 1139 of the handle 1130. The force applied to the pushbutton switch 1139 is here applied for example by a ramp 3147, i.e., indirectly. By the electromagnet 3139 or its movable core 3143, the test device 3000 may thus pretend that—instead of the test device 3000 actually inserted in the heparin pump 1000—a syringe 2000 is supposed to be inserted, which presses the pushbutton switch 1139 by its piston flange 2205. The electromagnet 3139 of FIG. 6 is exemplarily designed as a lifting magnet. Other designs and arrangements of an electromagnet are also encompassed by the present disclosure.

The electromagnet 3139 includes a coil 3141, which surrounds a movable core 3143. The plunger 3143 is mounted within a coil carrier 3145 and may be immersed in it, i.e., the plunger 3143 may be inserted against the restoring force R.

The restoring force R may be caused mechanically, for example by a spiral spring on electromagnet 3139 or by a restoring spring in the hinge 3149 of ramp 3147, as explained in more detail below.

If the coil 3141 of the electromagnet 3139 is supplied with electric voltage, the movable core 3143 is drawn or pulled into the coil carrier 3145 by the magnetic force M using the magnetic field of the coil 3141 against the restoring force R. The restoring force R and the magnetic force M are indicated by arrows in FIG. 6. The longer arrow illustrates that the magnetic force M must exceed the restoring forces R.

If this is the case, as shown in the right illustration in FIG. 6, the movable core 3143 presses with its end 3146 the optional ramp 3147, which in turn presses the pushbutton switch 1139. If the restoring force R has been overcome by the magnetic force M, caused by the coil 3141, the movable core 3143 presses with its end 3146 or the ramp 3147 onto the pushbutton switch 1139. In this case, the pushbutton switch 1139 emits the signal which it regularly emits whenever a syringe 2000 or its piston flange 2205 is in contact with it when using the pump 1000.

The ramp 3147, if provided, may be designed and arranged as a force transducer or converter, as in FIG. 6, in order to advantageously increase the force exerted by movable core 3143 according to the principle of the lever.

The ramp 3147 may be rotatably arranged for this purpose and may include for example a hinge 3149. The hinge 3149 or the ramp 3147 itself may exert a restoring force R, e.g., the hinge 3149 or the ramp 3147 may be equipped with a restoring spring or be sufficiently elastic. The restoring force returns the ramp 3147, and thus indirectly also the movable core 3143, to its starting position when the electromagnet 3139 is again free of electrical voltage or de-energized.

In the present example, the electromagnet 3139 itself does not have to have a reset device, e.g., a spring of its own, which is why it may be designed advantageously small.

The test device 3000, when assembled and attached to a heparin pump 1000, is able to simulate the presence of a syringe 2000 of a given diameter and to check the correct functioning of the pushbutton switch 1139 and the light barrier(s) of the wings 1121, 1123. The test device 3000 is, therefore, also able to provoke error messages from the dialysis apparatus 5000, for example by not (no longer) pressing the pushbutton switch 1139 or by moving the wings 1121, 1123 contrary to the assumption of the dialysis apparatus 5000. Failure to display the error messages provoked in this way may affect the test result.

As an alternative to the embodiment shown here, in which the electromagnet 3139 in its energized state actuates the pushbutton switch 1139, it may be provided that the electromagnet 3139, which is optionally usually designed unchanged, is arranged in such a way that it permanently actuates the pushbutton switch 1139 during its de-energized state using spring force. In this embodiment, the electromagnet 3139 must be energized in order to release the pushbutton switch 1139 as long as the electromagnet 3139 is energized. The pushbutton switch 1139 is therefore only actuated when the electromagnet 3139 does not receive current. The pushbutton switch 1139 is no longer actuated if and as long as the electromagnet 3139 is connected to the voltage source. With this design, permanent heating of the pushbutton switch 1139 and thus heat occurrence may advantageously be prevented. The energy consumption, as measured relative to the alternative described with reference to the figures, may also be reduced as a result.

Furthermore, subsequently or simultaneously, with regard to the heparin administration procedure described herein, by moving and braking the spindle 3103, heparin administration may be simulated using test device 3000 and, among other things, functions of the heparin pump 1000 and/or dialysis apparatus 5000 may also be tested, for example, the behavior in the event of stagnating thrust of the heparin pump 1000 due to the aforementioned blockage by the spindle drive 3100.

Figure 7:
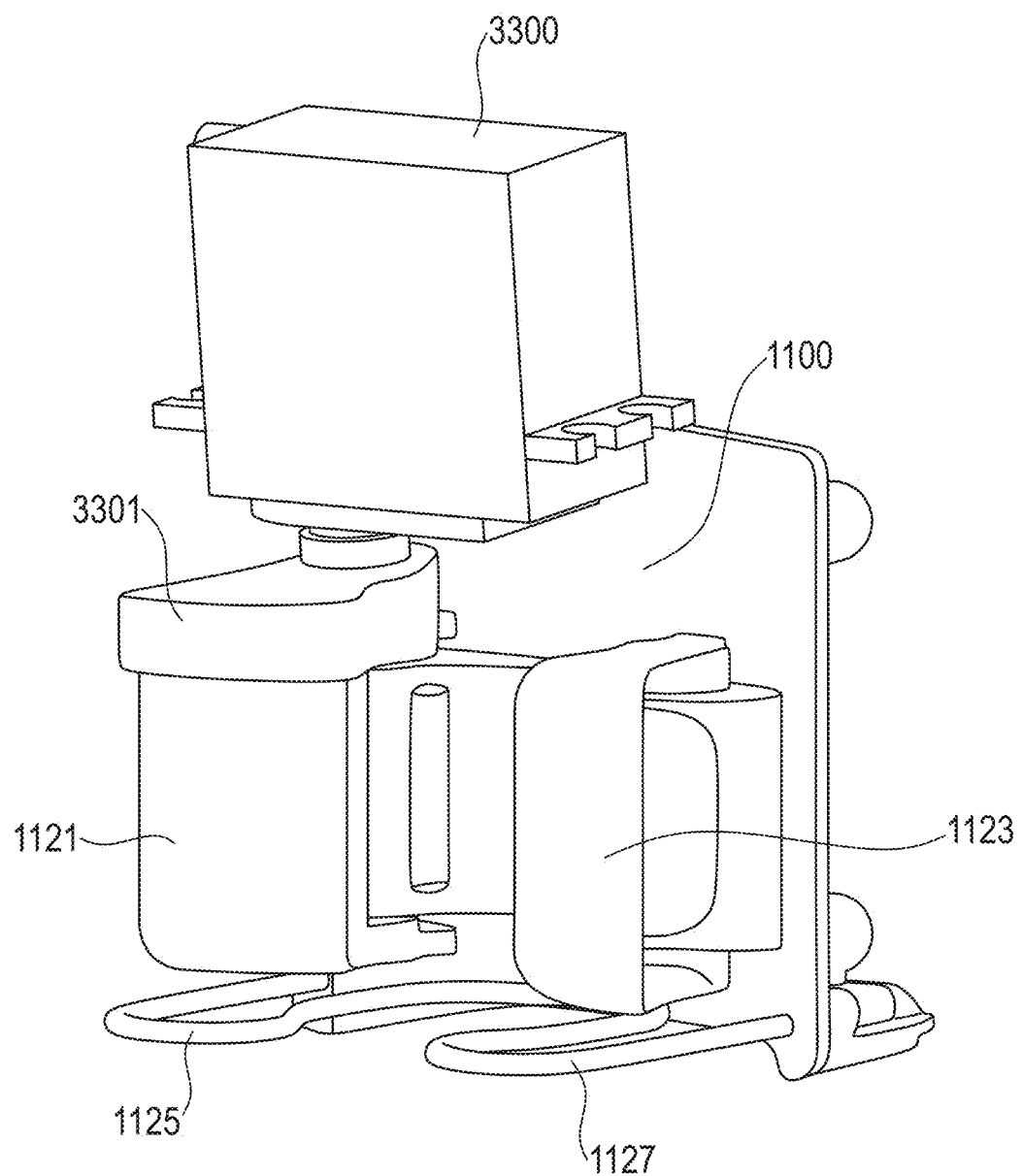
FIG. 7 shows the interaction of the first motor of FIG. 3 with one of the wings of FIG. 1.

FIG. 7 shows the interaction of the first motor 3300 of FIG. 3 with the wing 1121 of FIG. 1.

There is shown, a part of the syringe cavity 1100 of the heparin pump 1000 (which is not shown) of the dialysis apparatus 5000 (also not shown) with the brackets 1125, 1127, which are stationary in relation to the housing 5001, and the wings 1121, 1123, which are also immobile with respect to an up-down movement, which, however, are rotatable about their axes of rotation.

The first actuator 3301, optionally designed as a negative of the wing 1121, is placed on the left wing 1121. If the first actuator 3301 is rotated by the first motor 3300, the left wing 1121, which is releasably connected to it, also rotates about its axis of rotation As can be seen in FIG. 7, the first motor 3300 and thus also its motor shaft is optionally not straight but inclined against or relative to the vertical. This arrangement advantageously makes it possible to use a sufficiently large motor, the torque of which is sufficient to turn the wing 1121 against the return spring located inside the wing 1121. The slight inclination makes it possible, even for a comparatively large motor, to find space in the limited space available within the syringe cavity 1100.

Figure 8:
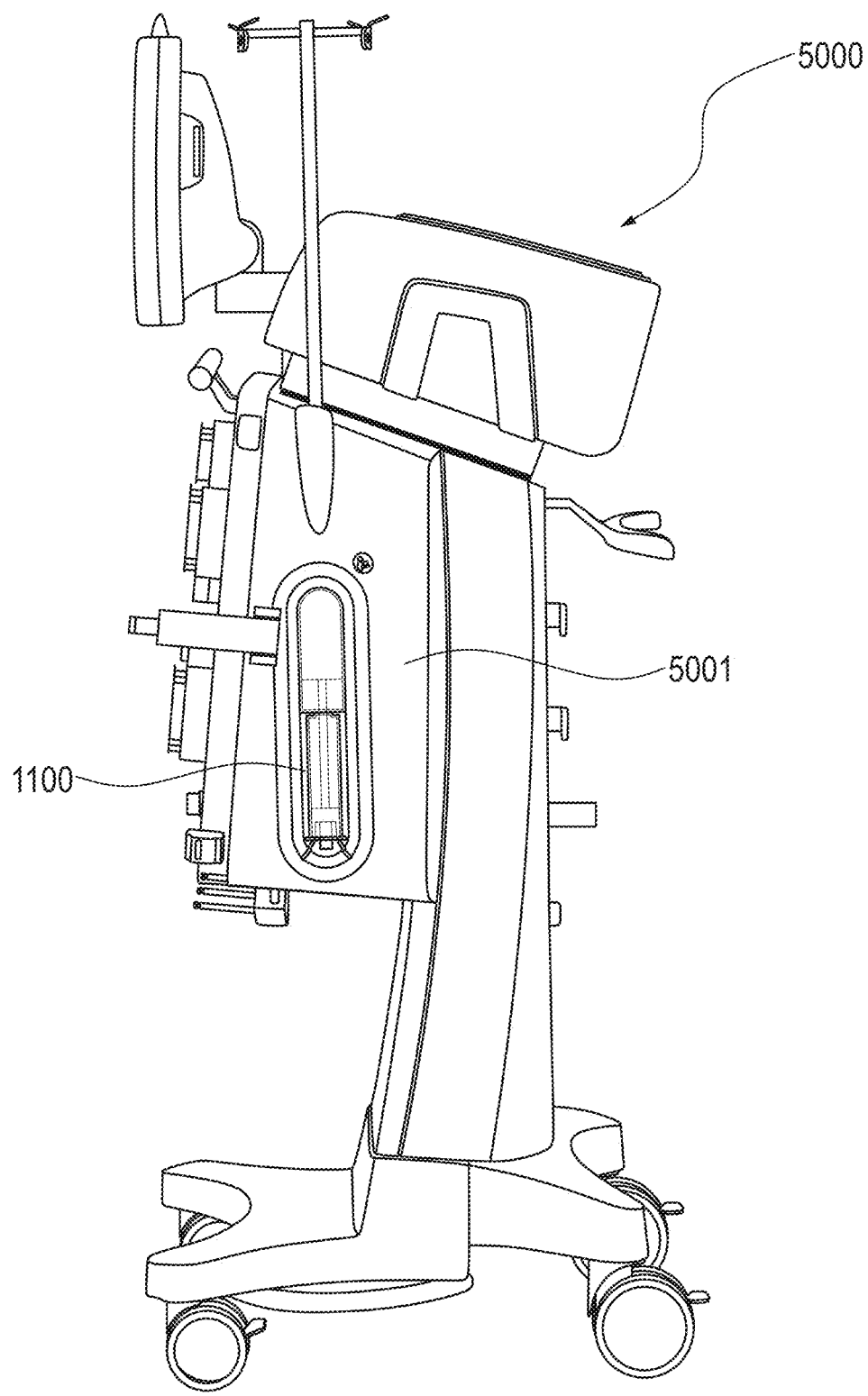
FIG. 8 shows a dialysis apparatus as part of a system as described herein.

FIG. 8 shows the dialysis apparatus 5000 as part of the system described herein. The syringe cavity 1100 already shown in the previous figures can be seen.

Figure 9:
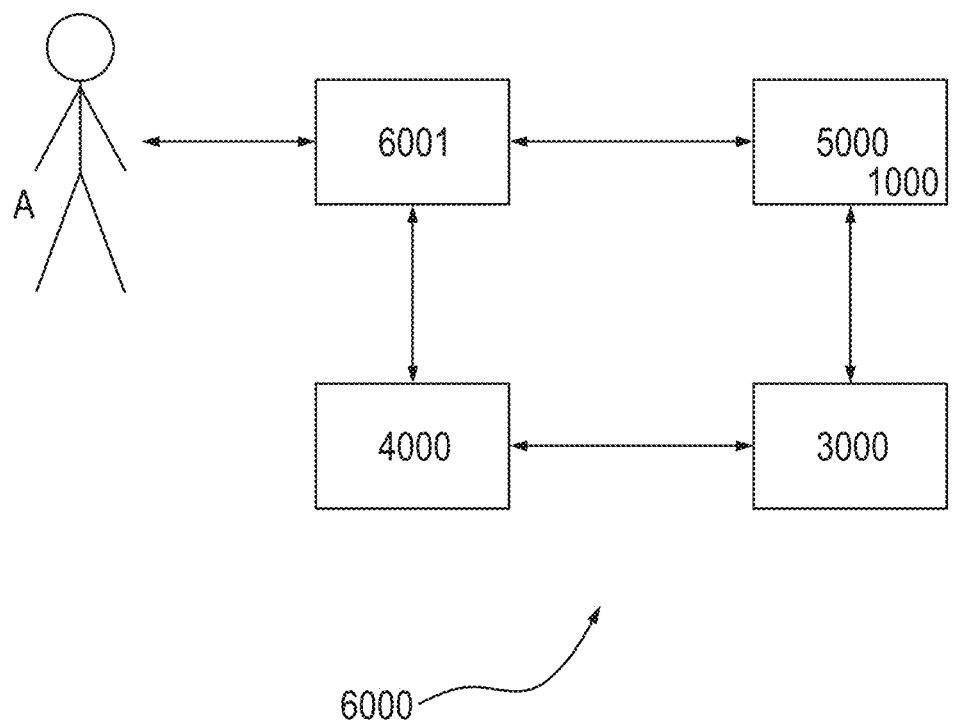
FIG. 9 shows schematically simplified a further embodiment of a system.

FIG. 9 shows a system 6000 in a further embodiment.

A user A has the possibility to use an input device (not shown in FIG. 9) to inform or instruct a computer 6001 which functions of pump 1000 of blood treatment apparatus 5000 are to be checked by the test device 3000. The input device may, for example, include or be a smartphone or another wireless input device, or an input device of the computer 6001, for example a monitor and/or a keyboard.

The functions to be tested are converted into test commands by the computer 6001.

For this purpose, a so-called "Testcase Execution Tool" (TET) may be implemented and used on the computer 6001 in some embodiments. The TET is a program with which test cases may be automatically simulated under computer control. For this purpose, the test schemes and/or scenarios with the corresponding test commands are written, for example, in a ready-made or pre-made Excel sheet. The language and form may be based on the Python programming language, but it can also be operated by people without programming knowledge.

In certain embodiments, the TET or the computer 6001 in general may communicate with the blood treatment apparatus 5000, for example, via a Controller Area Network adapter, or CAN adapter in short. The CAN adapter may thus be understood in connection with the TET as an interface between computer 6001 and blood treatment apparatus 5000. The CAN adapter is illustrated in FIG. 9 as a double arrow between the computer 6001 and the blood treatment apparatus 5000.

With optional, active communication with the blood treatment apparatus 5000 via the optional CAN adapter and corresponding software, variables or parameters may be set, read and/or overwritten. This may also help to simulate fault or error conditions without having to manipulate the sensors.

In some embodiments, existing test schemes may be transmitted or translated into TET format from other software, for example from a visualization tool that may be used to influence variables.

After the test scheme has been written and stored using the TET, the test scheme may be started using an input device, for example the console of the blood treatment apparatus 5000. The test scheme is then processed automatically and the corresponding test is performed. After all test commands of the test scheme are finished (or even earlier), a feedback about the test result may be given. If the expected results deviate from the test results, it is possible, for example, to record when and/or where the deviation occurred. The results may be logged and/or saved, for example in a text file, so that they can be accessed at any time.

The test commands are transmitted to the test device 3000 via the control device 4000, which may also be a signal transmission device. The control device 4000 may be integrated in and/or in signal communication with the test device 3000.

By the test commands, the test device 3000 is able to process predetermined test tasks of individual or all motors 3100, 3139, 3300, 3400 of the test device 3000, on the basis of which functions of the pump 1000 and/or of the blood treatment apparatus 5000 in connection with its pump 1000 are tested for correct performance In some embodiments, the test device 3000 is designed to return a feedback and/or a test result via the control device 4000 to the computer 6001, for example in the form of output signals. The output signals may then be converted again by the computer 6001 into outputs which are understandable for the user A which may then be output as the test result, for example via an output device (not shown in FIG. 9) such as a monitor or also via a mobile terminal (e.g., a smartphone).

In some embodiments, the findings of the blood treatment apparatus 5000, e.g., through output devices (display, protocol, alarms, etc.) are of interest in order to be able to assess the correct functioning of the blood treatment apparatus 5000 and/or the pump 1000, e.g., in a (simulated) error situation.

The above-mentioned, respectively optional, signal paths are all represented by double arrows in FIG. 9.

Figure 10:
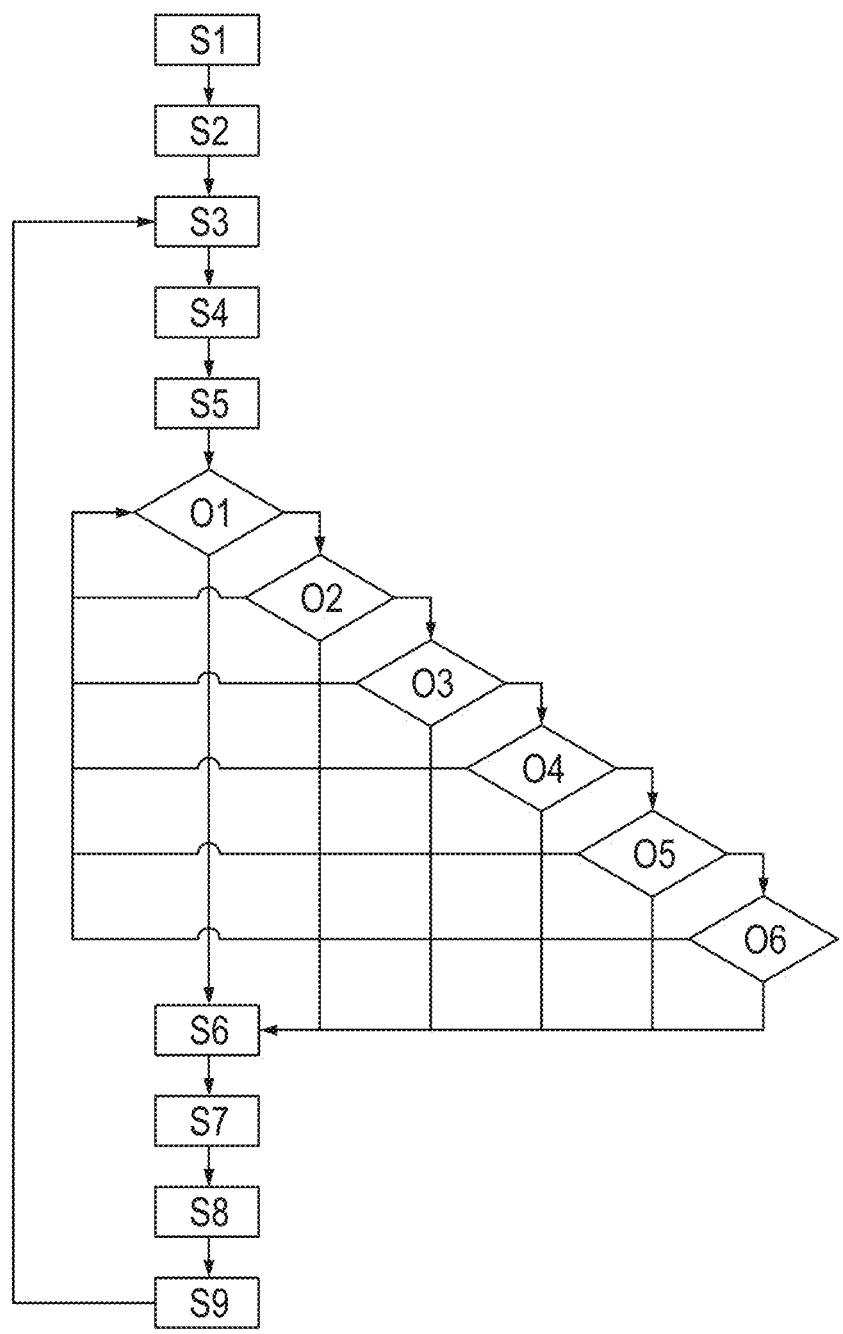
FIG. 10 shows a flowchart of an embodiment of a method as described herein.

FIG. 10 shows a flowchart of the method for testing at least one function of a pump 1000 and/or of a blood treatment apparatus 5000 with a pump 1000 in an exemplary embodiment.

The method, for example, includes:

Step S1 represents providing a system 6000 as described herein.

In step S2 the test device 3000 is inserted into the syringe receptacle 1100 of the pump 1000.

In step S3, it may optionally be determined by the computer 6001 which functions of the pump 1000 or of the blood treatment apparatus 5000 are to be checked or tested by the test device 3000, for example via an input device of the computer 6001 (e.g., a smartphone). The determination may be carried out by a user A, for example by clicking, selecting, etc. The determination may be predetermined, for example programmed, and/or lead to an automatic execution of the test. The determination may be stored/programmed in the computer 6001 or in the control device 4000.

In step S4, the blood treatment apparatus 5000 is activated or actuated to cause or bring about an activity of the pump 1000 which is to be checked.

Controlling the control device 4000 of the test device 3000 is carried out by the computer 6001 in step S5. The following cascade of optional controls O1 to O6, which may also be understood as test commands, represents the possibilities of common, separate, simultaneous, or successive control of some or all motors 3100, 3139, 3300, 3400 of the test device 3000. According to these possibilities, a test command generated by the computer 6001 may be executed.

In this case, the arrows after step S6 represent the transfer by the blood treatment apparatus 5000 or the pump 1000 or the (possibly automatic) query of parameters by the computer 6001.

The arrows to the right each represent the selection of a different or a next step or test command. It may always be possible to return to one of the previous steps or test commands.

As an example here, the supply of current or voltage to the electromagnet 3139 (see O3) is or may be mentioned, for example in order to check the function of the pushbutton switch 1139 and/or the processing of a signal coming from the pushbutton switch 1139, by the blood treatment apparatus 5000.

It may be advantageous, after successful testing of the pushbutton switch 1139 by activating the electromagnet 3139, to subsequently disconnect it from the current. Accordingly, control O4 could follow control O3. This optional recursion is represented by the arrows that leave the diamond of controls O1 to O6 to the left.

The following types of optional controls are represented by the cascade of FIG. 10:

O1 stands for the control of the spindle drive 3100 to turn the spindle 3103 in a first direction of rotation and thus move the carrier 3200, for example, towards the wings 1121, 1123 of the pump 1000. In this way, a conveying may be simulated according to or beyond the set value(s). O2 stands for the control of the spindle drive 3100 in order to rotate the spindle 3103 in an opposite, second direction of rotation and thereby move the carrier 3200 in a second direction, which may be defined away from the wings 1121, 1123 of the pump 1000, for example. This may simulate conveying against the set or usual conveying direction.

O3 stands for the supply of current or voltage to electromagnet 3139 in order to directly or indirectly trigger an operation of the pushbutton switch 1139 by the electromagnet 3139.

O4 stands for disconnecting the electromagnet 3139, which previously actuated the pushbutton switch 1139, from a current or from a voltage in order to directly or indirectly end an actuation of the pushbutton switch 1139.

O5 stands for the control of the first motor 3300 in order to turn at least one of the wings 1121 around its axis of rotation by the first actuator 3301. The pump 1000 or the blood treatment apparatus 5000 recognizes that, depending on the angle of rotation of the wing 1121, a syringe 2000 with the corresponding diameter, e.g., 30 ml, 50 ml, etc., is inserted. O5 may be understood as a result of checking whether the light barrier correctly indicates the syringe diameter imitated by the first actuator 3301, which could be indicated by the blood treatment apparatus 5000 or output as a parameter by it.

O6 stands for the control of the second motor 3400 in order to operate at least one of the clamping levers 1135, 1137 of the pump 1000 by the second actuator 3401 to decouple the pump spindle 1103 of pump 1000 from the handle 1130 of pump 1000. This may be necessary in order to separate the handle 1130, in which a position sensor may be present, from its positive coupling with the pump spindle 1103 in order to enable the handle 1130 and its position sensor to be moved solely by the pump spindle 3103 according to O1 or O2. In particular, the optional control O6 may be used in parallel with one or more of the other optional controls O1 to O5.

Step S6 may be understood as data collection. Here, values and results from the optional controls O1 to O6 are collected, i.e., stored and/or made available. This step may be performed in or by the blood treatment apparatus 5000.

In step S7, parameters may be queried or read from the blood treatment apparatus 5000, which describe which activity the pump 1000 undertakes, according to the understanding of the blood treatment apparatus 5000, or which error has been detected. The parameters may include the results of an adjustment which the blood treatment apparatus 5000 optionally performs. Alternatively or in addition, these may be parameters which are output by the blood treatment apparatus 5000 in connection with the operation or activity of the pump 1000. The parameters may be, e.g., measurement results, error messages, alarms, status reports, etc. The query may be made using the computer 6001 or the output devices of the blood treatment apparatus 5000 or of the pump 1000.

In step S8, the queried parameters are optionally evaluated on the basis of predetermined criteria which may evaluate the test results and make them understandable for the user. The evaluation may include simple mathematical operations such as the calculation of sums, differences, products and/or quotients. The evaluation may be a check of results or values, for example truth values. The evaluation may be a comparison with expected values or expected results.

In step S9, the evaluation is optionally output to a user, for example via an output device of the computer 6100, or a mobile data device, for example a smartphone.

In some embodiments, it is possible to return to step S3, i.e., to make a further input of functions to be tested, which restarts the method.

In some embodiments, the method may also be carried out automatically, i.e., without the intervention of the user A.

In some embodiments, the method may start and/or end fully automatically by placing the test device 3000 at the pump 1000 or at the blood treatment apparatus 5000 and thereby detecting its connection to the pump 1000 or to the blood treatment apparatus 5000, e.g., by a pressure switch present on the test device 3000. The test device 3000 in these embodiments may be configured to fully automatically execute a (pre-)determined test scheme with the corresponding test commands and then to transmit the determined results to the computer 6001 or to output them to user A by the output devices of said computer when said test device 3000 has detected its connection to the pump and executed the (predetermined) test scheme.

Whenever a suitability or a method step is mentioned herein, the present disclosure also encompasses corresponding programming or configuration of a suitable apparatuses or a section thereof.

LIST OF REFERENCE NUMERAL

1000 heparin syringe pump, heparin pump, pump
1100 syringe cavity; syringe receptacle
1101 pump drive
1103 pump spindle
1105 draw tube
1120 syringe holder
1121 wing
1123 wing
1125 bracket
1127 bracket
1130 handle
1131 clip
1133 clip
1135 clamping lever 1137 clamping lever
1139 pushbutton switch
2000 syringe; heparin syringe
2201 syringe cylinder
2203 cylinder flange
2205 piston flange
2207 syringe piston
2209 piston stopper or plug
2211 nozzle
3000 test device
3100 spindle drive
3101 coupling
3103 spindle
3105 draw tube
3107 fastening
3109 fastening
3139 electromagnet
3141 coil
3143 movable core
3145 coil carrier
3146 end of the movable core
3147 ramp
3149 hinge
3200 carrier
3300 first motor
3301 first actuator
3400 second motor
3401 second actuator
3402 fastening
3403 receptacle for clamp lever 1135
3405 receptacle for clamp lever 1137
3407 rotary section
3409 spherical section
3411 spherical section
3500 holder
3501 slot
3503 slot
4000 control device
5000 blood treatment apparatus; dialysis apparatus
5001 housing
6000 system
6001 computer
A user
R restoring force
M magnetic force
O1 to O6 optional controls; test commands
S1 to S8 step methods

The invention claimed is:

1. A syringe pump testing system for testing at least one function of a syringe pump of a blood treatment apparatus, the system comprising:
   a syringe pump comprising:
   a pump drive;
   a pump spindle;
   a handle arranged to abut a piston flange of a syringe when the syringe is engaged with the syringe pump, wherein the pump spindle is in rotary connection with the pump drive and is connected in a form-fit and/or force-fit manner to the handle so that when the pump spindle is rotated by the pump drive the handle is displaced translationally;
   a clamping arrangement comprising a first spring and two clips, the clamping arrangement configured for clamping the piston flange between the two clips using spring force of the first spring, the clamping arrangement further comprising at least one clamping lever that is operable for releasing the clamping against the spring force when actuated;
   two wings and a second spring, the two wings configured for receiving a section of a cylinder of a syringe between them and against spring force of the second spring; and
   a pushbutton switch arranged to be pressed on by a piston flange of a syringe that is inserted into the clamping arrangement;
   a test device comprising:
   a holding device configured for releasably holding the test device on a surface of a blood treatment apparatus;
   a movable actuator; and
   at least one electric motor arranged to directly or indirectly rotate or translate the movable actuator or a section thereof, the at least one electric motor comprising a spindle drive; and
   a computer configured for generating and/or transmitting at least one test command to:
   read parameters from the blood treatment apparatus; and/or
   rotate the pump spindle in a first direction of rotation using the spindle drive; and/or
   rotate the pump spindle in a second direction of rotation opposite to the first direction of rotation using the spindle drive; and/or
   rotate at least one of the wings about its axis of rotation using a first motor of the at least one electric motor and a first actuator of the movable actuator; and/or
   actuate, using a second motor of the at least one electric motor and a second actuator of the movable actuator, the at least one clamping lever of the pump for decoupling the pump spindle from the handle of the pump; and/or
   directly or indirectly actuate and/or release the pushbutton switch using an electromagnet; and/or
   wherein a control device is in signal communication with the computer.

2. A system according to claim 1, wherein the test device is, or is provided to be, mounted on at least one bracket of the blood treatment apparatus.

3. A method for testing at least one function of a pump and/or of a blood treatment apparatus comprising a pump, the method comprising:
   providing a system according to claim 1;
   inserting the test device into the syringe receptacle of the pump;
   actuating the blood treatment apparatus to cause or effect an activity or operation of the pump;
   actuating the control device by the computer in order to execute one or more test commands, generated by the computer, including the following commands:
   actuating the spindle drive to rotate the spindle in a first direction of rotation in order to move a section being connected to the spindle in a first direction of movement, wherein the first direction of movement is defined towards the wings of the pump;
   actuating the spindle drive to rotate the spindle in a second direction of rotation in order to move a section being connected to the spindle, in a second direction of movement, wherein the second direction of movement is defined away from the wings of the pump;
   blocking or stopping the spindle drive in order to simulate a standstill of the pump;

supplying the electromagnet with current or voltage in order to directly or indirectly trigger or terminate, using the electromagnet, an actuation of the pushbutton switch;

disconnecting or releasing the electromagnet previously actuating the pushbutton switch from current or voltage in order to terminate or trigger an actuation of the pushbutton switch;

actuating the first motor to rotate at least one of the wings about its axis of rotation using the first actuator;

actuating the second motor in order to actuate, using the second actuator, at least one of the clamping levers of the pump for decoupling the pump spindle of the pump from the handle of the pump; and retrieving from the blood treatment apparatus parameters which describe the activity of the pump and/or querying or reading out parameters which are output by the blood treatment apparatus in connection with the activity of the pump.

4. The method according to claim 3, further comprising entering, via an input device, at least one test command or one function of the pump or of the blood treatment apparatus to be tested, by a user and assigning one or more test commands.

5. The method according to claim 3, wherein the one or more test commands further include evaluating the retrieved parameters based on predetermined criteria.

6. The method according to claim 5, wherein the one or more test commands further include outputting a result of the evaluation using an output device.

7. The method according to claim 5, wherein the evaluation comprises calculating sums, differences, products, and/or quotients, checking results or values, and/or a comparing with expected values or expected results.

8. The method according to claim 3, wherein at least one of the one or more test commands is automatically executed.

9. A pump tested by the method according to claim 3.

10. A blood treatment apparatus comprising the pump according to claim 9.

* * * * *